US011033683B2

(12) United States Patent
Helmer et al.

(10) Patent No.: US 11,033,683 B2
(45) Date of Patent: Jun. 15, 2021

(54) MEDICAMENT INJECTION DEVICE

(71) Applicant: SANOFI-AVENTIS DEUTSCHLAND GMBH, Frankfurt am Main (DE)

(72) Inventors: Michael Helmer, Frankfurt am Main (DE); Winfried Huthmacher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 245 days.

(21) Appl. No.: 15/779,060

(22) PCT Filed: Nov. 21, 2016

(86) PCT No.: PCT/EP2016/078273
§ 371 (c)(1),
(2) Date: May 24, 2018

(87) PCT Pub. No.: WO2017/089283
PCT Pub. Date: Jun. 1, 2017

(65) Prior Publication Data
US 2018/0339106 A1    Nov. 29, 2018

(30) Foreign Application Priority Data

Nov. 27, 2015  (EP) .................................... 15196708

(51) Int. Cl.
*A61M 5/20* (2006.01)
*A61M 5/24* (2006.01)
(Continued)

(52) U.S. Cl.
CPC ............ *A61M 5/20* (2013.01); *A61M 5/2466* (2013.01); *A61M 5/3287* (2013.01);
(Continued)

(58) Field of Classification Search
CPC .. A61M 2005/2414; A61M 2005/2474; A61M 2005/2496; A61M 5/2455;
(Continued)

(56) References Cited

U.S. PATENT DOCUMENTS 2,392,196 A * 1/1946 Smith ................. A61M 5/2448
604/91
3,825,003 A * 7/1974 Kruck ................. A61M 5/288
604/192
(Continued)

FOREIGN PATENT DOCUMENTS

CN          103269730          8/2013
CN          103687636          3/2014
(Continued)

OTHER PUBLICATIONS

PCT International Preliminary Report on Patentability in International Appln. No. PCT/EP2016/078273, dated May 29, 2018, 7 pages.
(Continued)

*Primary Examiner* — Shefali D Patel
(74) *Attorney, Agent, or Firm* — Fish & Richardson P.C.

(57) ABSTRACT

A medicament injection device comprising: a needle holder holding a needle, a pivotable cartridge holder, the pivotable cartridge holder being pivotable from an open state to a closed state, wherein the pivotable cartridge holder is arranged to receive a medicament cartridge in the open state, and wherein the needle holder is axially movable towards the pivotable cartridge holder when the pivotable cartridge holder is in the closed state.

21 Claims, 11 Drawing Sheets

(51) Int. Cl.
*A61M 5/32* (2006.01)
*A61M 5/315* (2006.01)

(52) U.S. Cl.
CPC ....... *A61M 5/31533* (2013.01); *A61M 5/3202* (2013.01); *A61M 2005/202* (2013.01); *A61M 2005/206* (2013.01); *A61M 2005/2013* (2013.01); *A61M 2005/2073* (2013.01); *A61M 2005/2414* (2013.01); *A61M 2005/2474* (2013.01); *A61M 2005/2496* (2013.01)

(58) Field of Classification Search
CPC ............. A61M 5/2459; A61M 5/2466; A61M 5/3202; A61M 5/20; A61M 5/24; A61M 5/3287; A61M 5/3293; A61M 2005/2006; A61M 2005/202; A61M 2005/206; A61M 2005/2073; A61M 2005/2403; A61M 2005/2485
See application file for complete search history.

(56) References Cited

U.S. PATENT DOCUMENTS

| | | | | |
|---|---|---|---|---|
| 5,545,145 | A * | 8/1996 | Clinton | A61M 5/002 206/366 |
| 7,828,778 | B2 * | 11/2010 | Liversidge | A61M 5/3205 604/198 |
| 8,206,351 | B2 * | 6/2012 | Sugimoto | A61M 5/20 604/151 |
| 9,662,457 | B2 | 5/2017 | Reynolds et al. | |
| 10,201,659 | B2 | 2/2019 | Kaufmann et al. | |
| 2004/0210197 | A1 | 10/2004 | Conway | |
| 2013/0138048 | A1 * | 5/2013 | Kemp | A61M 5/2033 604/196 |
| 2014/0081234 | A1 | 3/2014 | Eggert et al. | |

FOREIGN PATENT DOCUMENTS

| | | |
|---|---|---|
| EP | 2799056 | 11/2014 |
| JP | H11-33114 | 2/1999 |
| JP | 2013-532522 | 8/2013 |
| JP | 2014-519384 | 8/2014 |
| WO | WO 2009/091707 | 7/2009 |
| WO | WO 2012/012603 | 1/2012 |
| WO | WO 2012/158135 | 11/2012 |
| WO | WO 2012/160156 | 11/2012 |
| WO | WO 2013/063707 | 5/2013 |
| WO | WO 2014/076225 | 5/2014 |
| WO | WO 2014/080020 | 5/2014 |
| WO | WO 2014/091765 | 6/2014 |
| WO | WO 2015/018787 | 2/2015 |
| WO | WO 2015/059201 | 4/2015 |
| WO | WO 2015/117854 | 8/2015 |

OTHER PUBLICATIONS

PCT International Search Report and Written Opinion in International Appln. No. PCT/EP2016/078273, dated Feb. 13, 2017, 9 pages.

* cited by examiner

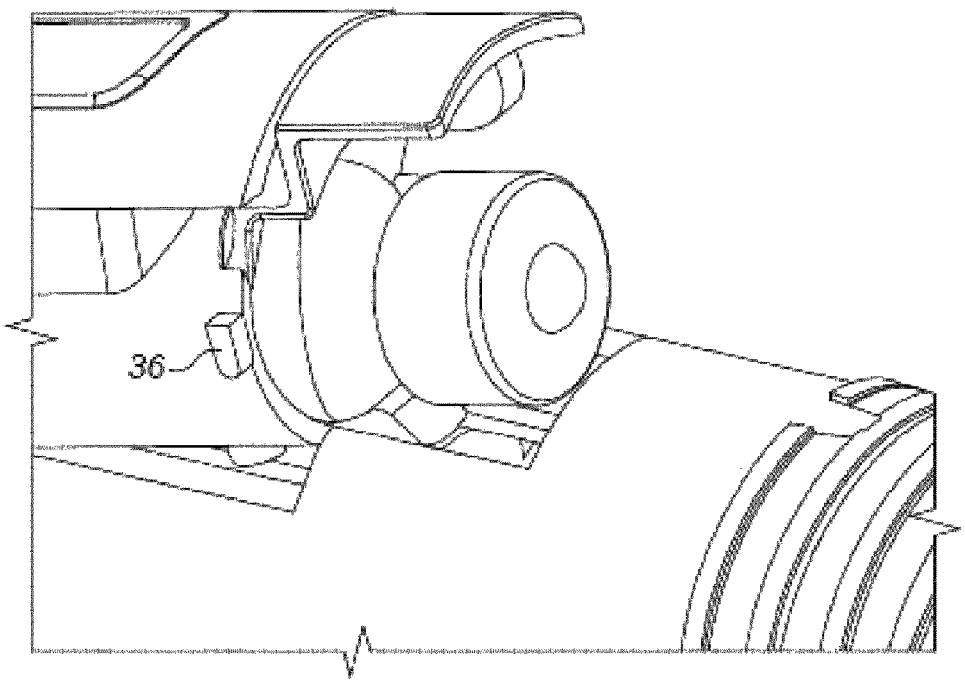
FIG. 10A
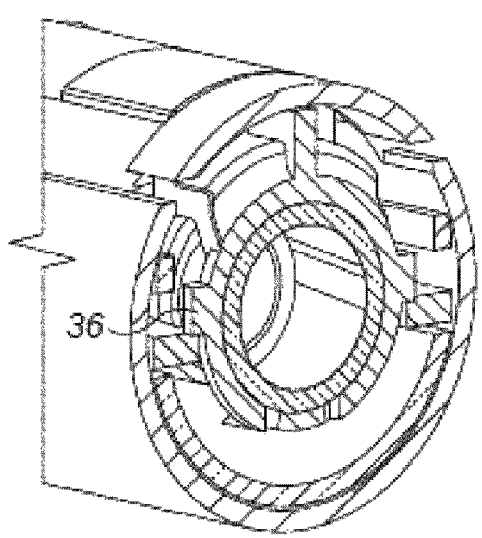 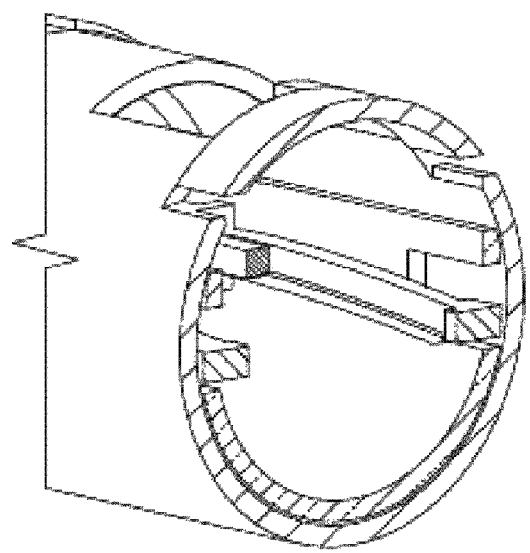
FIG. 10B
FIG. 10C

MEDICAMENT INJECTION DEVICE

CROSS REFERENCE TO RELATED APPLICATIONS

The present application is the national stage entry of International Patent Application No. PCT/EP2016/078273, filed on Nov. 21, 2016, and claims priority to Application No. EP 15196708.0, filed on Nov. 27, 2015, the disclosures of which are incorporated herein by reference.

TECHNICAL FIELD

The present disclosure relates to medicament injection devices.

BACKGROUND

Medicament injection devices can take various forms. One form of injection device uses a medicament cartridge. Typically, a patient connects a double-ended needle to the cartridge before injection, thereby piercing the cartridge's seal with the proximal tip of the double-ended needle.

While a cartridge can provide handling and storage advantages relative to syringes, they are not without shortcomings. For example, the attachment of a needle to the cartridge requires an additional step. This step can be problematic for patients with limited dexterity, poor coordination, or who have lost a degree of sensation in their hands. Even with such disadvantages, in certain situations it is desirable to provide an injection device in which the needle is kept separate from the medicament until such time as the patient wishes to commence the injection. The injection device described herein aims to overcome one or more problems associated with prior devices.

SUMMARY

A first embodiment provides a medicament injection device comprising:
  a needle holder holding a needle,
  a pivotable cartridge holder, the pivotable cartridge holder being pivotable from an open state to a closed state,
  wherein the pivotable cartridge holder is arranged to receive a medicament cartridge in the open state, and wherein the needle holder is axially movable towards the pivotable cartridge holder when the pivotable cartridge holder is in the closed state, and
  wherein movement of the pivotable cartridge holder to the closed state causes axial movement of the needle holder in a proximal direction towards the cartridge holder.

The pivotable cartridge holder may be pivotable about a bearing axis towards the proximal end.

The device may further comprise a needle sleeve and a pre-stressed spring coupled to the needle sleeve and the needle holder, wherein movement of the pivotable cartridge holder to the closed state causes a release of the pre-stressed spring, thereby causing the axial movement of the needle holder towards the cartridge holder.

The device may further comprise a cap and a needle sleeve, wherein the cap is coupled to the needle sleeve and comprises a clip to prevent removal of the cap until the spring is released.

The device may further comprise one or more clips arranged to prevent accidental closure of the pivotable cartridge holder.

The device may further comprise a clip configured to secure the pivotable cartridge holder to the main body of the device subsequent to closing the pivotable cartridge holder.

The device may further comprise a needle shield for protecting a distal end of the needle.

The device may further comprise a solid foil for protecting a proximal end of the needle.

The device may further comprise a compressible spacer to protect the solid foil.

The pivotable cartridge holder may contain a cartridge containing a medicament.

The device may be an auto-injector.

A second embodiment provides a method of loading a medicament injection device comprising a needle holder holding a needle, the method comprising: inserting a medicament cartridge having a penetrable barrier at one end thereof into a pivotable medicament cartridge holder; and closing the pivotable medicament cartridge holder; wherein closing the pivotable medicament cartridge holder causes axial movement of the needle holder towards the cartridge holder and causes the needle to penetrate the penetrable barrier.

BRIEF DESCRIPTION OF THE FIGURES

Exemplary embodiments of the present disclosure are described with reference to the accompanying drawings, in which:

FIG. 10A is a close up view of the medicament cartridge holder and medicament cartridge in an open state;

FIG. 10B is a close up cross-sectional view of the medicament cartridge holder and medicament cartridge in a closed state;

FIG. 10C is a simplified close up cross-sectional view of the medicament cartridge holder and medicament cartridge in a closed state;

DETAILED DESCRIPTION

Figure 1:
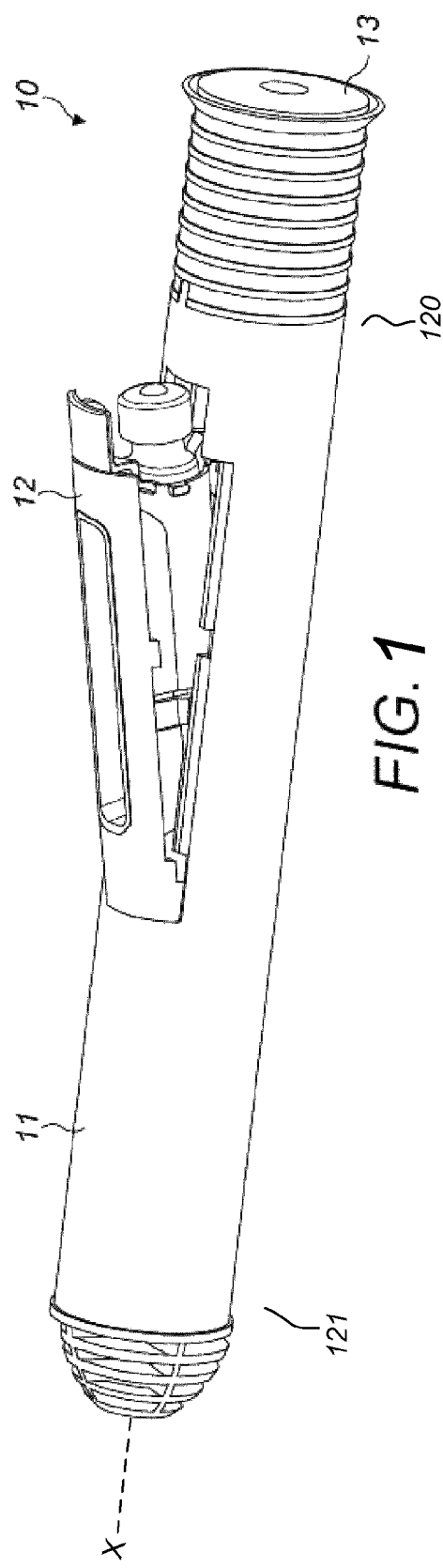
FIG. 1 is a side-on view of a device according to a first embodiment.

Embodiments of the present disclosure provide a mechanism for inserting a medicament cartridge into a pivotable cartridge holder of an injection device. The needle of the injection device can then be inserted into the cartridge containing a medicament for injection by a patient or care giver after the pivotable cartridge holder has been closed. The mechanism allows the medicament cartridge to remain sealed until such time as the user wishes to commence the injection.

An advantage of these embodiments is that the medicament contained within the cartridge is not in constant contact with the needle during storage of the device. This can prevent clogging of the medicament around the tip of the needle.

A pivotable cartridge holder provides a guide for the user to insert the cartridge when the pivotable cartridge holder is open.

Automating a mechanism for inserting the needle into the medicament cartridge after the pivotable cartridge holder has been closed also reduces the amount of handling of the needle by the user prior to the injection. Indeed, in some embodiments described below, the user does not touch the needle when the needle is inserted into the medicament cartridge. In some embodiments, the needle is prevented from being moved until the pivotable cartridge holder has been closed.

In embodiments of the disclosure the needle is initially coupled to a cap of the device and is isolated during storage (i.e. after manufacture and before use).

The steps of storing the device and subsequently inserting the needle into the medicament cartridge can be performed without exposing the needle.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 2:
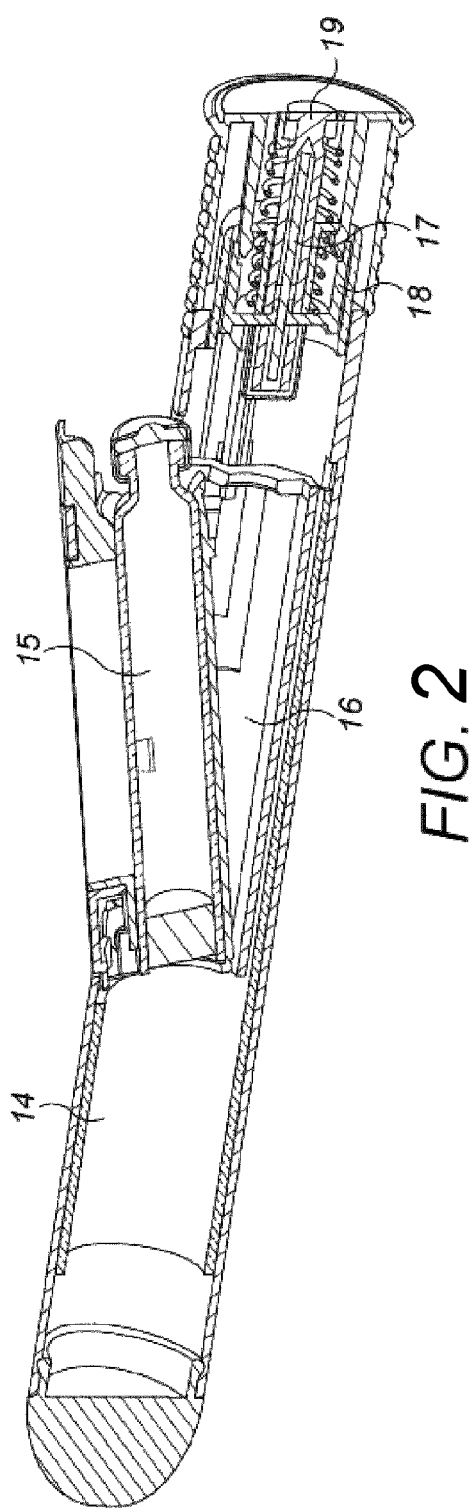
FIG. 2 is a cross-sectional view of the device shown in FIG. 1.

According to some embodiments of the present disclosure, an exemplary drug delivery device 10 is shown in FIGS. 1 and 2. Device 10, as described above, is configured to inject a medicament into a patient's body. Device 10 includes a body 11 which typically contains a reservoir containing the medicament to be injected (e.g., a syringe) and the components required to facilitate one or more steps of the delivery process. Device 10 can also include a cap assembly 13 that can be detachably mounted to the body 11. Typically a user must remove cap 13 from body 11 before device 10 can be operated.

As shown, body 11 is substantially cylindrical and has a substantially constant diameter along the longitudinal axis X. The body 11 has a distal region 120 and a proximal region 121. The term "distal" refers to a location that is relatively closer to a site of injection, and the term "proximal" refers to a location that is relatively further away from the injection site.

Device 10 can also include a needle sleeve 14 coupled to body 11 to permit movement of sleeve 14 relative to body 11. For example, sleeve 14 can move in a longitudinal direction parallel to longitudinal axis X. Specifically, movement of sleeve 14 in a proximal direction can permit a needle 17 to extend from distal region 120 of body 11.

Insertion of needle 17 can occur via several mechanisms. For example, needle 17 may be fixedly located relative to body 11 and initially be located within an extended needle sleeve 14. Proximal movement of sleeve 14 by placing a distal end of sleeve 14 against a patient's body and moving body 11 in a distal direction will uncover the distal end of needle 17. Such relative movement allows the distal end of needle 17 to extend into the patient's body. Such insertion is termed "manual" insertion as needle 17 is manually inserted via the patient's manual movement of body 11 relative to sleeve 14.

Another form of insertion is "automated," whereby needle 17 moves relative to body 11. Such insertion can be triggered by movement of sleeve 14 or by another form of activation, such as, for example, an activation button. The button may be located at a proximal end of body 11. However, in other embodiments, the button could be located on a side of body 11.

Other manual or automated features can include drug injection or needle retraction, or both. Injection is the process by which a bung or piston is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 121 of body 11, and a distal end of the drive spring can be configured to apply a compressive force to a proximal surface of piston. Following activation, at least part of the energy stored in the drive spring can be applied to the proximal surface of piston. This compressive force can act on piston to move it in a distal direction. Such distal movement acts to compress the liquid medicament within the syringe, forcing it out of needle 17.

Following injection, needle 17 can be retracted within sleeve 14 or body 11. Retraction can occur when sleeve 14 moves distally as a user removes device 10 from a patient's body. This can occur as needle 17 remains fixedly located relative to body 11. Once a distal end of sleeve 14 has moved past a distal end of needle 17, and needle 17 is covered, sleeve 14 can be locked. Such locking can include locking any proximal movement of sleeve 14 relative to body 11.

Another form of needle retraction can occur if needle 17 is moved relative to body 11. Such movement can occur if the syringe within body 11 is moved in a proximal direction relative to body 11. This proximal movement can be achieved by using a retraction spring (not shown), located in distal region 120. A compressed retraction spring, when activated, can supply sufficient force to the syringe to move it in a proximal direction. Following sufficient retraction, any relative movement between needle 17 and body 11 can be locked with a locking mechanism. In addition, button or other components of device 10 can be locked as required.

The device 10 comprises a generally cylindrical hollow tubular body 11, a pivotable cartridge holder 12 and a cap 13.

FIG. 2 is a cross-sectional view of the device 10 shown in FIG. 1. The device 10 further comprises a generally tubular needle sleeve 14 which is located inside the main body 11 and extends coaxially therewith. The cartridge holder 12 contains a medicament cartridge 15. The device 10 comprises a carrier 16 arranged to receive the cartridge holder 12 when the cartridge holder 12 is closed by a user after the medicament cartridge 15 has been inserted. The device 10 may be provided, in appropriate packaging, to the user with the medicament cartridge 15 already inserted. Alternatively, the medicament cartridge 15 may be provided separately to be inserted by the user prior to commencing the injection.

The device 10 comprises a needle 17 held by a needle holder 18. The distal end of the needle is shielded by a needle shield 19. A pre-stressed spring 20 is also provided to assist with insertion of the proximal end of the needle 17 into the medicament cartridge 15.

Figure 3:
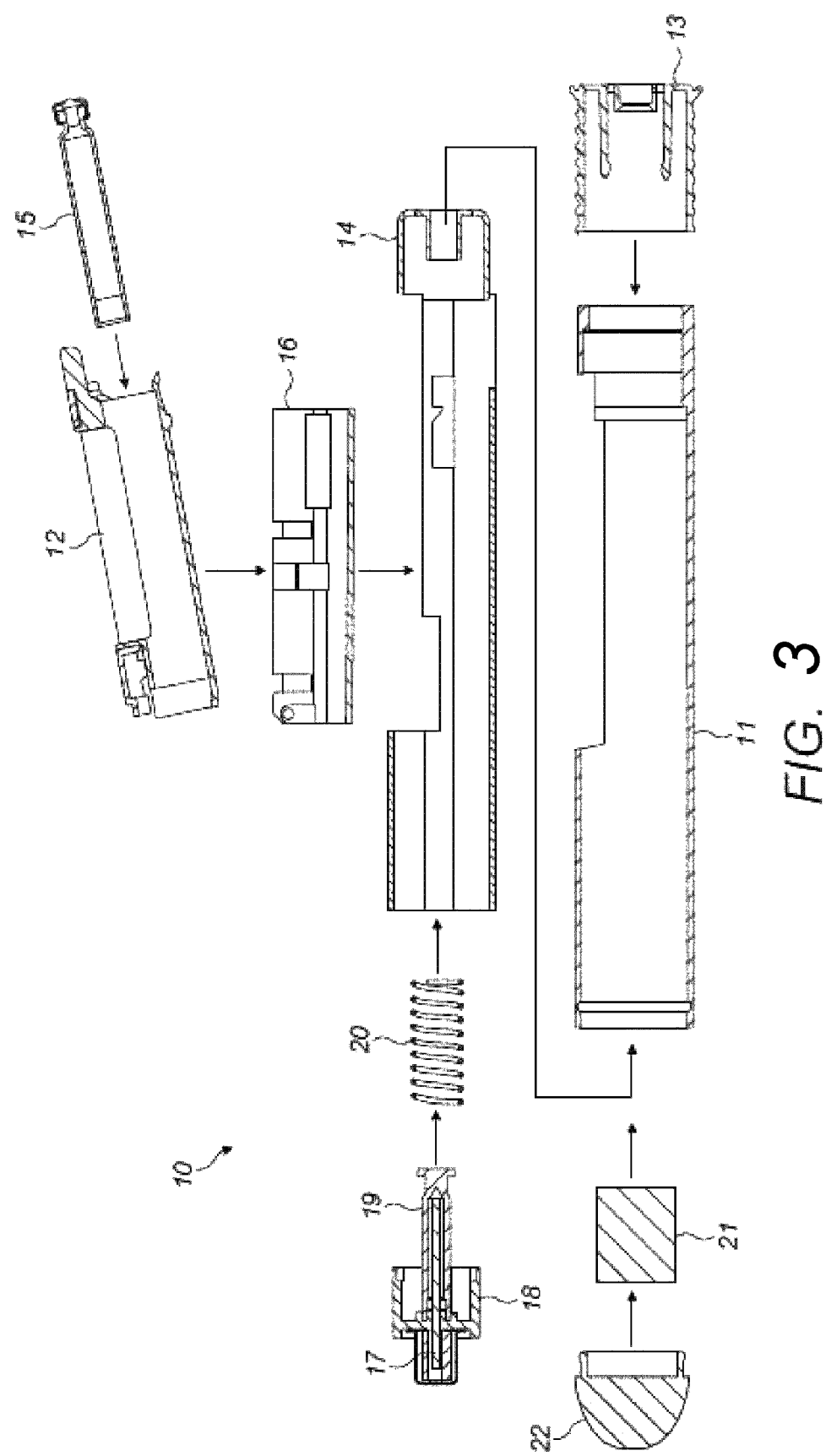
FIG. 3 is a side-on cross-sectional view of components of the device.

FIG. 3 is a cross-sectional view of the components of the device 10 prior to assembly of the device 10. The device 10 comprises a power pack 21 and a body end cap 22.

Figure 4A:
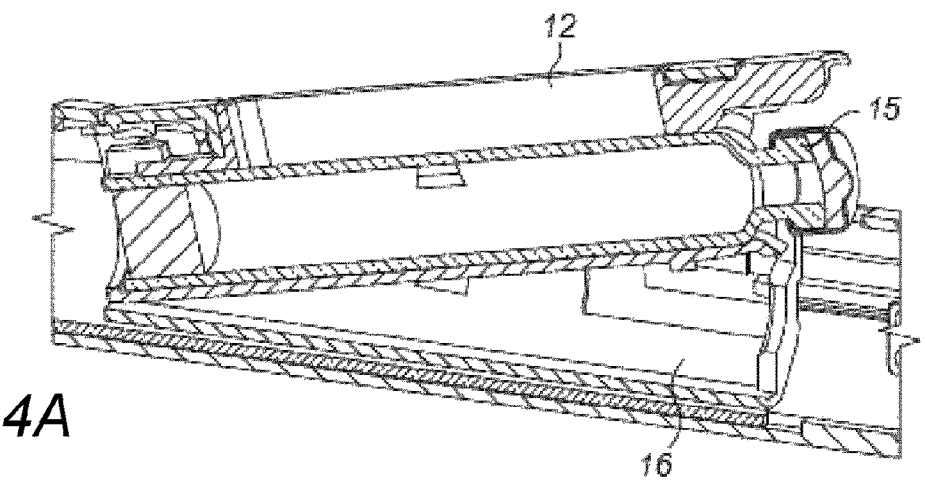
FIG. 4A is a close-up cross-sectional view of a medicament cartridge.
Figure 4B:
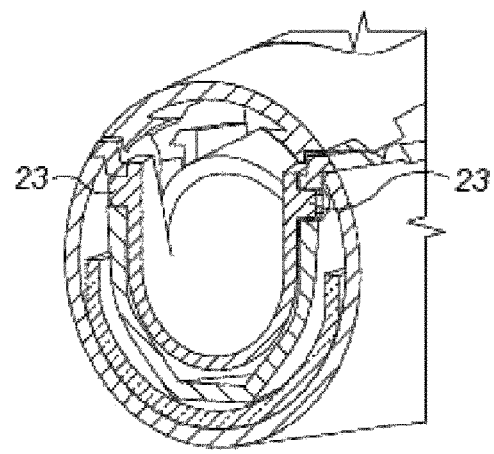
FIG. 4B is a close-up cross-sectional view of the proximal end of a cartridge holder.
Figure 4C:
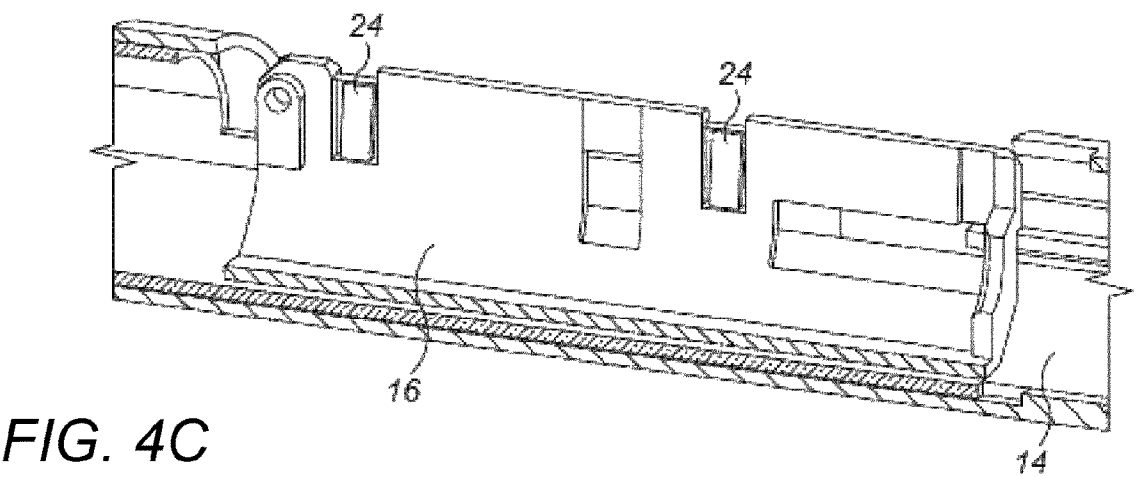
FIG. 4C is a close-up cross-sectional view of a carrier.

FIG. 4A is a cross sectional view of the part of the device 10 containing the cartridge holder 12, medicament cartridge 15 and carrier 16. FIG. 4B shows the pivot points 23 about which the cartridge holder 12 pivots relative to the carrier 16 which is fixed with respect to the needle sleeve 14. FIG. 4C shows clips 24 which fix the carrier 16 to the body 11. As such, the pivot points are situated on a bearing axis transverse to the longitudinal axis X of the device 10 towards the proximal end of the device 10.

Figure 5A:
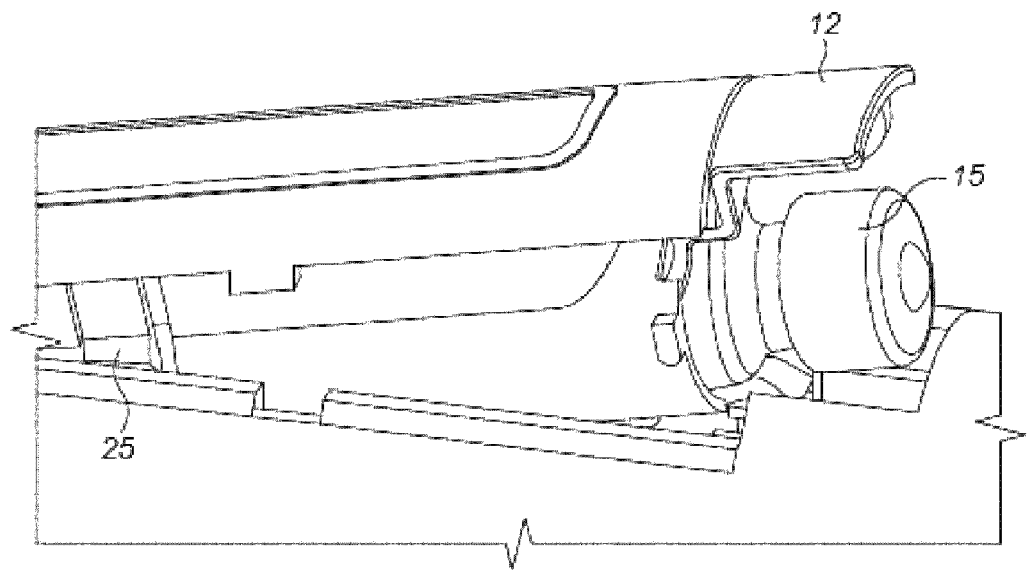
FIG. 5A is a close-up view of the medicament cartridge holder and medicament cartridge.
Figure 5B:
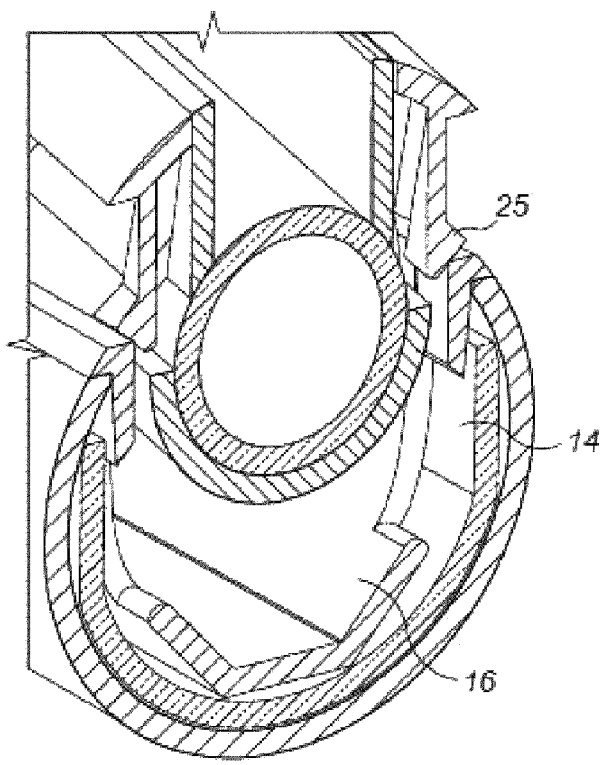
FIG. 5B is a close-up cross-sectional view of the medicament cartridge holder and medicament cartridge.

FIG. 5A is a close-up view of the cartridge holder 12 and cartridge 15. The cartridge holder 12 comprises cartridge holder clips 25. The clips 25 have a tapered surface that allow the clips 25 to slide past the carrier 16 as the cartridge holder 12 is closed. Prior to closing the cartridge holder 12, the clips 25 provide sufficient resistance to provide tactile feedback to the user so that the user is less likely to close the cartridge holder 12 accidentally. The clips 25 also have a stepped surface (see FIG. 5B) so that, after the cartridge holder 12 has been moved to the closed position, the clips 25 prevent subsequent pivotal movement of the cartridge holder 12 to the open position shown in FIG. 1. As such, the step of closing the cartridge holder 12 is not reversible.

Figure 6A:
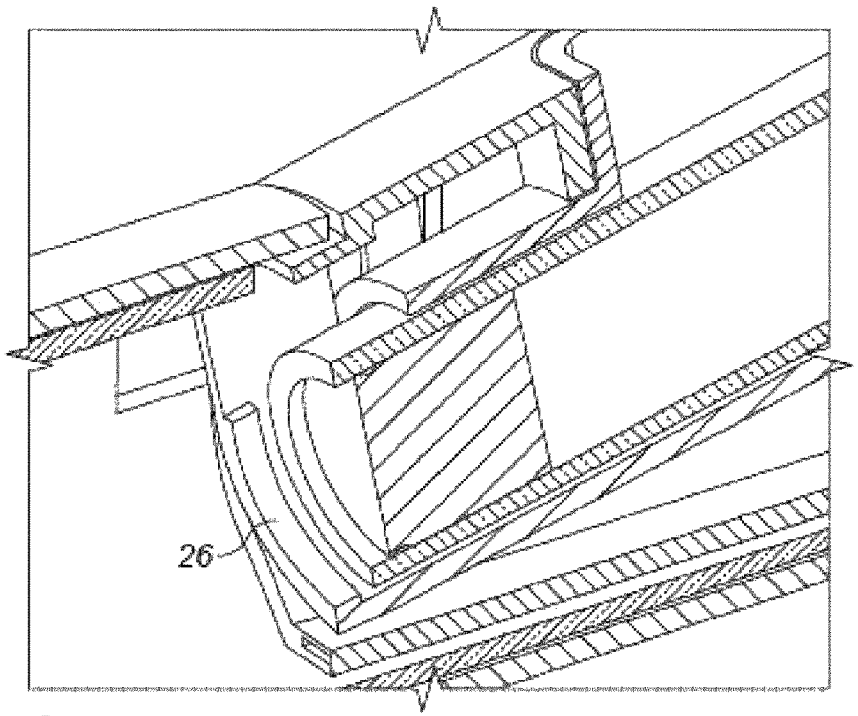
FIG. 6A is a close-up cross-sectional view of the proximal end of the medicament cartridge holder and medicament cartridge.

FIG. 6A shows a close-up of the proximal end of the cartridge holder 12. The cartridge holder 12 comprises an end stop 26 to support the proximal end of the medicament cartridge 15. The end stop 26 defines the position of a piston prior to commencement of the injection.

Figure 6B:
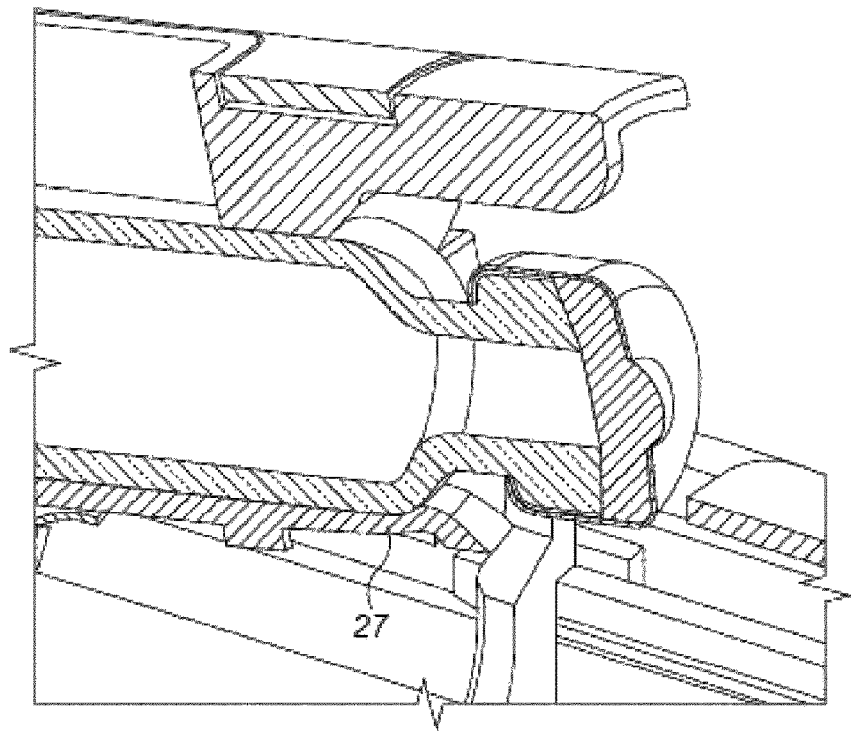
FIG. 6B is a close-up cross-sectional view of the distal end of the medicament cartridge holder and medicament cartridge.

FIG. 6B shows a close-up of the distal end of the cartridge holder 12. The cartridge holder 12 comprises a distal end clip 27 to support the distal end of the medicament cartridge 15.

Figure 7:
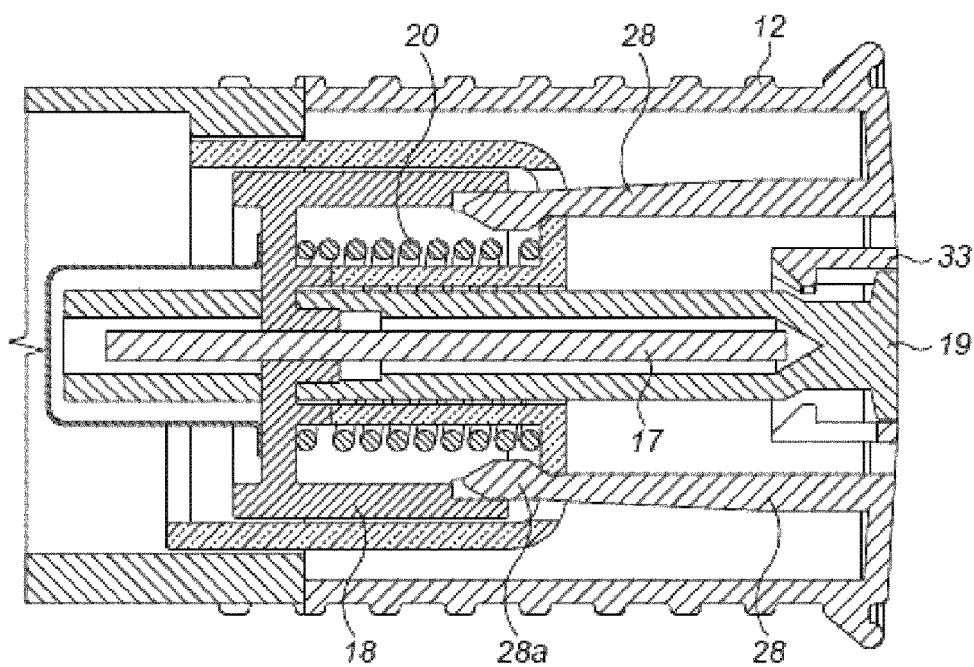
FIG. 7 is a close-up cross-sectional view of the cap assembly.

FIG. 7 shows a close-up cross sectional view of the distal end of the device 10. The cap 12 comprises arms 28 that are each provided with expanded end parts or hooks 28a at a proximal end thereof. Each of the arms 28 are supported on an inner surface by the needle sleeve 14 and on an outer surface by the needle holder 18. Removal of the cap 12 from the device 10 is prevented since the hooks 28a prevent the cap 12 being pulled in an axial direction. As explained below, the cap can only be removed after the needle 17 and the needle holder 18 have been inserted into the medicament cartridge 15. Needle shield clips 33 are provided to ensure that the needle shield 19 is removed as the cap 12 is removed.

Figure 8A:
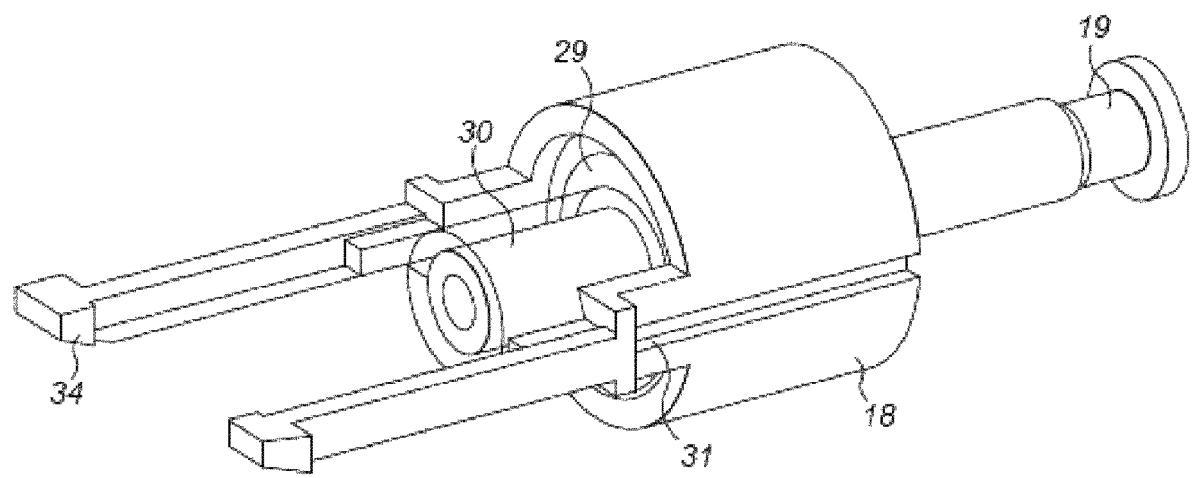
FIG. 8A is a close up view of a needle assembly.

FIG. 8A shows the needle assembly comprising the needle holder 18, the needle shield 19, solid foam 29, spacer 30, guide link 31, arms 34 as well as the needle which is not shown in this figure. The needle shield 19 shields the distal end of the needle 17 to provide sterility until such time as it is removed prior to the injection. The solid foil 29 is provided to protect and to provide sterility to the proximal end of the needle 17. The spacer 30 may be formed from foam and is provided to protect the solid foil 29 from damage by the needle 17. The guide link 31 is provided to guide axial movement of the needle holder in the sleeve 14.

Figure 8B:
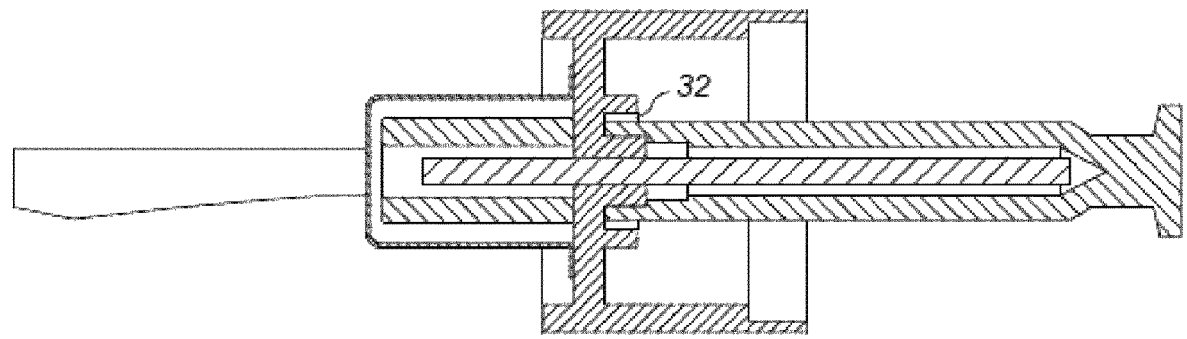
FIG. 8B is a close up cross-sectional view of a needle assembly.

FIG. 8B is a cross-sectional view of the needle assembly. A sealed connection 32 is provided between the needle holder 18 and needle shield 19. Sterility of the proximal end of the needle 17 is ensured by the solid foil 29 which may be welded or glued to the needle holder 18.

Figure 9:
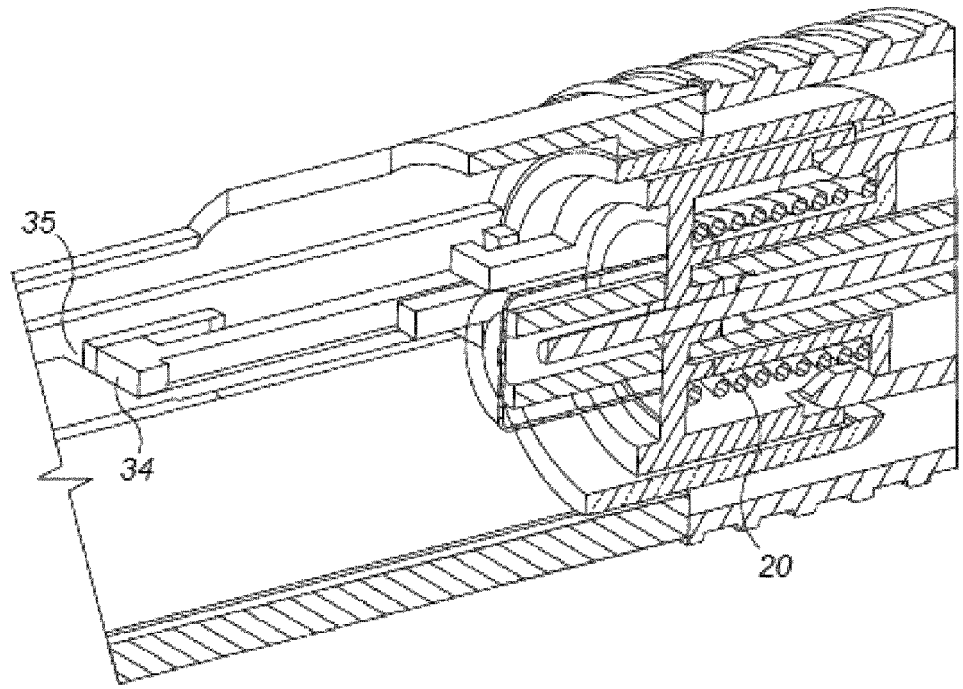
FIG. 9 is a close up cross-sectional view of the cap and needle assemblies.

FIG. 9 shows the interface between the needle sleeve 14 and the needle holder 18 before the spring has been released. The proximal ends of the arms 34 are supported by protrusions 35 located on the needle sleeve 14. The protrusions 35 prevent premature axial movement of the needle holder 18 towards the medicament cartridge 15.

FIG. 10A shows an ear 36 located on the distal end of the cartridge holder 12 when the cartridge holder 12 is in the open position. FIGS. 10B and 10C show the device 10 after the cartridge holder 12 has been moved to the closed position. The ear 36 pushes against the arms 34 which, in turn, causes the arms 34 to disengage from the protrusions 35, thereby releasing the spring 20. In FIG. 10C some of the components have been removed for illustrative purposes.

Figure 11:
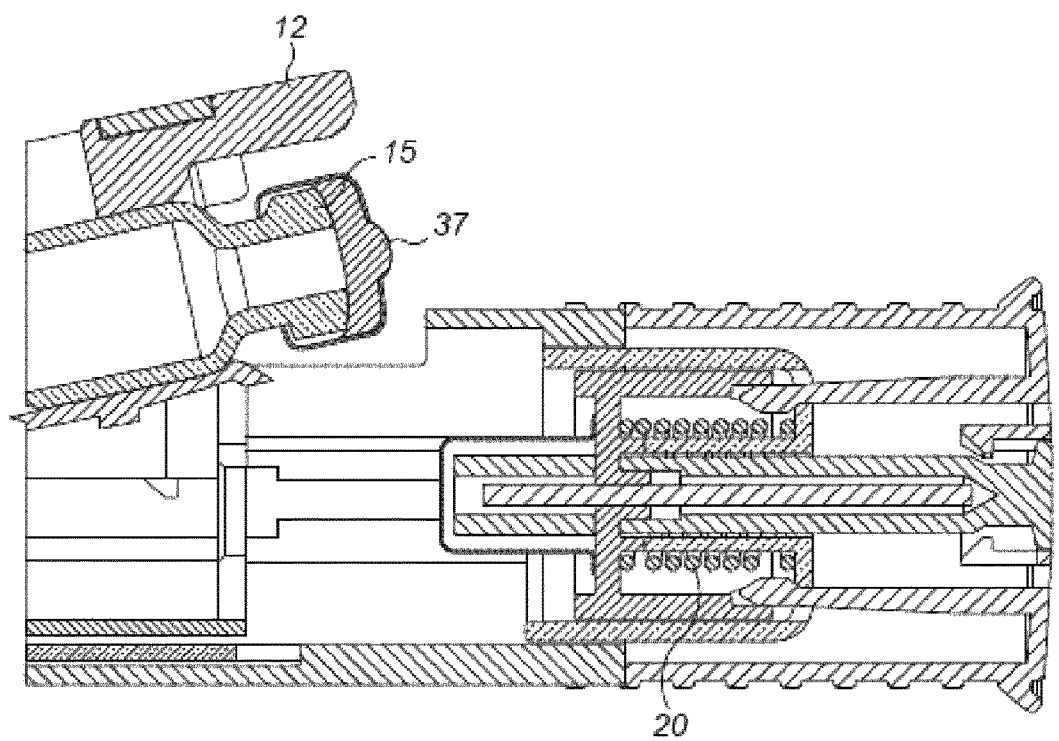
FIG. 11 is a close up cross-sectional view of the cap assembly and the proximal end of the medicament cartridge holder and medicament cartridge in an open state.

FIG. 11 shows a cross-sectional view of the distal end of the device 10 prior to closure of the cartridge holder 12. The spring 20 is in its pre-stressed position. Furthermore, the cap 12 cannot be removed since it is held in place by the needle holder 18 and the needle sleeve 14.

Figure 12:
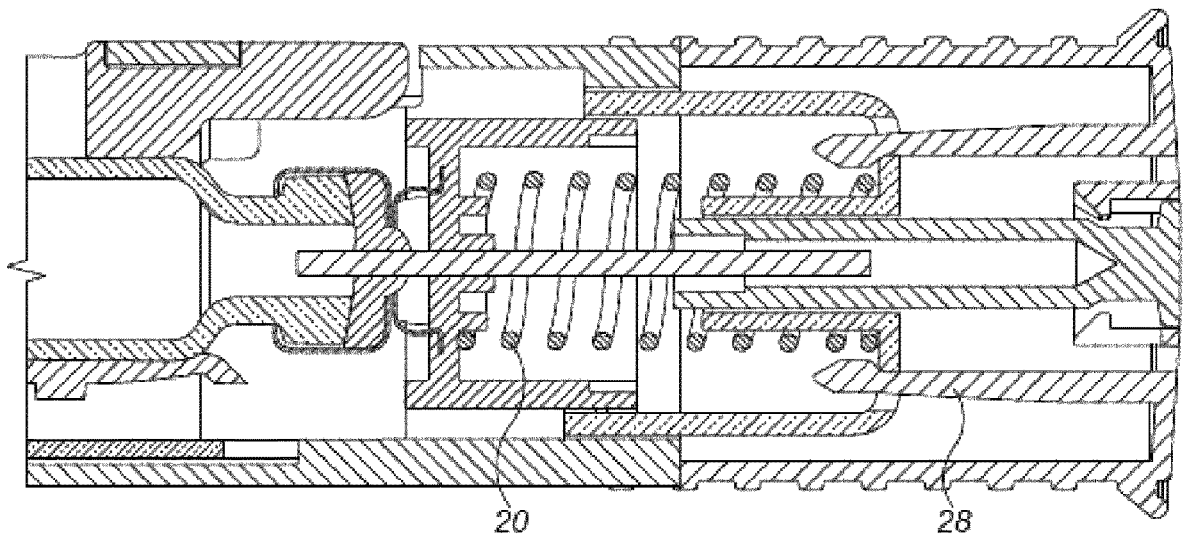
FIG. 12 is a close up cross-sectional view of the cap assembly and the proximal end of the medicament cartridge holder and medicament cartridge as the needle is inserted into the cartridge.

FIG. 12 shows the device 10 after the cartridge holder 12 has been closed. As explained above with reference to FIG. 10B, the spring 20 is released. The release of the spring 20 causes the needle holder to be pushed towards a proximal end of the device 10. The movement of the needle holder 18 causes a compression of the spacer 30. The proximal end of the needle 17 is caused to pierce a septum 37 of the medicament cartridge 15. Furthermore, the arms 28 of the cap 12 are no longer supported by the needle holder 18. Thus, it is possible to remove the cap 12 from the device. Once the cap has been removed, the injection may be commenced.

The injection may be commenced by pushing the distal end of the device 10 against the patient's skin which causes exposure of the distal end of the needle 17.

Figure 13:
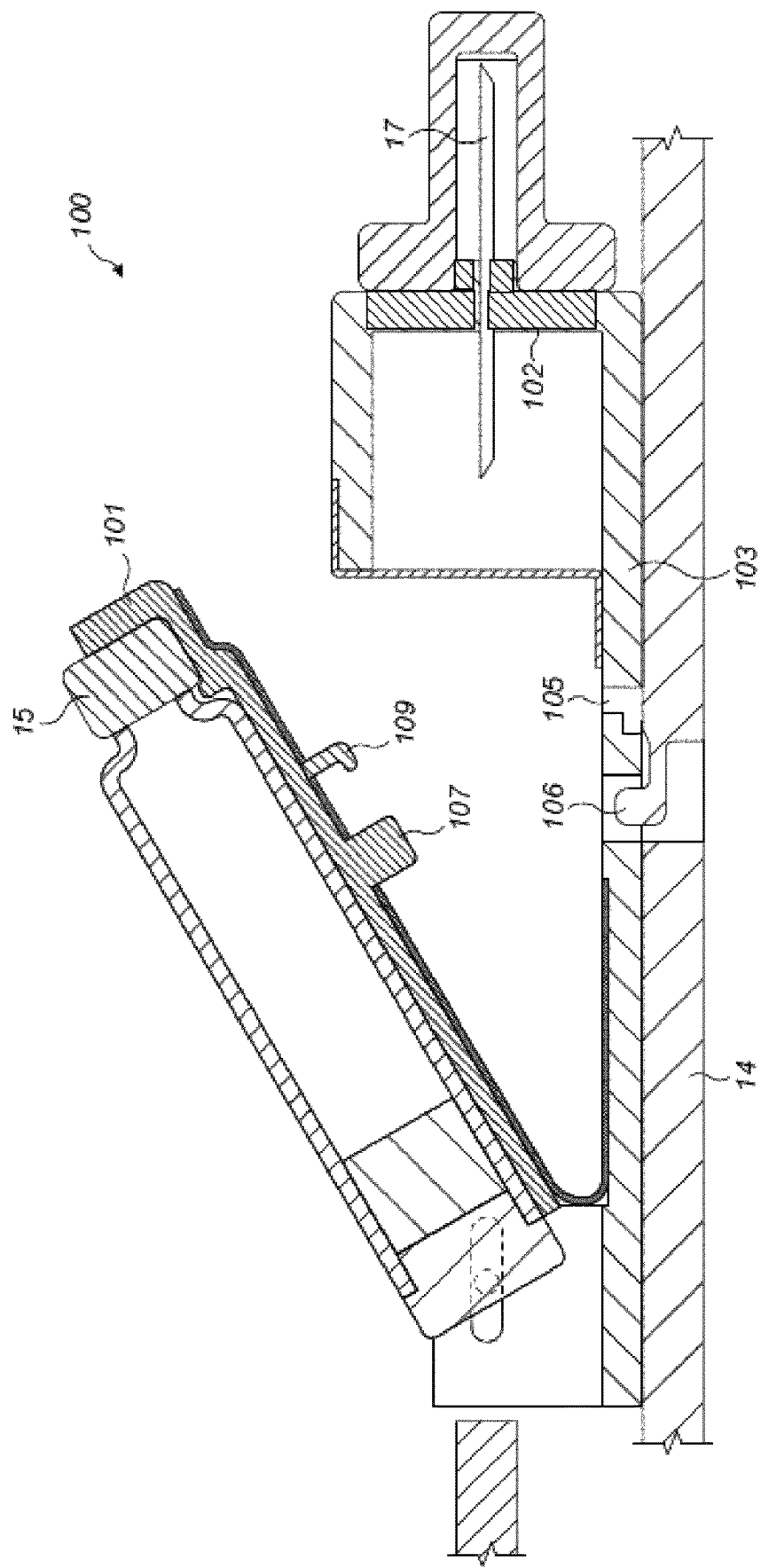
FIG. 13 is a simplified cross-sectional view of a device according to an alternative embodiment in an open state.

FIG. 13 shows a simplified cross-sectional diagram of a device 100 according to an alternative embodiment. The device 100 comprises a pivotable cartridge holder 101 configured to receive a cartridge 15 and an axially movable needle holder 102 holding a needle 17. The device 100 comprises a carrier 103 configured to receive the pivotable cartridge holder 101 in its closed position. The pivotable cartridge holder 101 has a hook 104 which may be received by a recess 105 provided in the carrier 103. Once the pivotable cartridge holder 101 has been closed, the hook 104 is received by the recess 105 and may not be removed. Thus closing the pivotable cartridge holder 101 is an irreversible step.

The needle sleeve 14 is provided with a locking member 106 that engages with a corresponding recess provided in the carrier 103. As shown in FIG. 13, the needle sleeve 14 may not move relative to the carrier 103 or main body of the device 100. The cartridge holder 101 has an unlocking member 107 for disengaging the needle sleeve 14 from the carrier 103.

Figure 14:
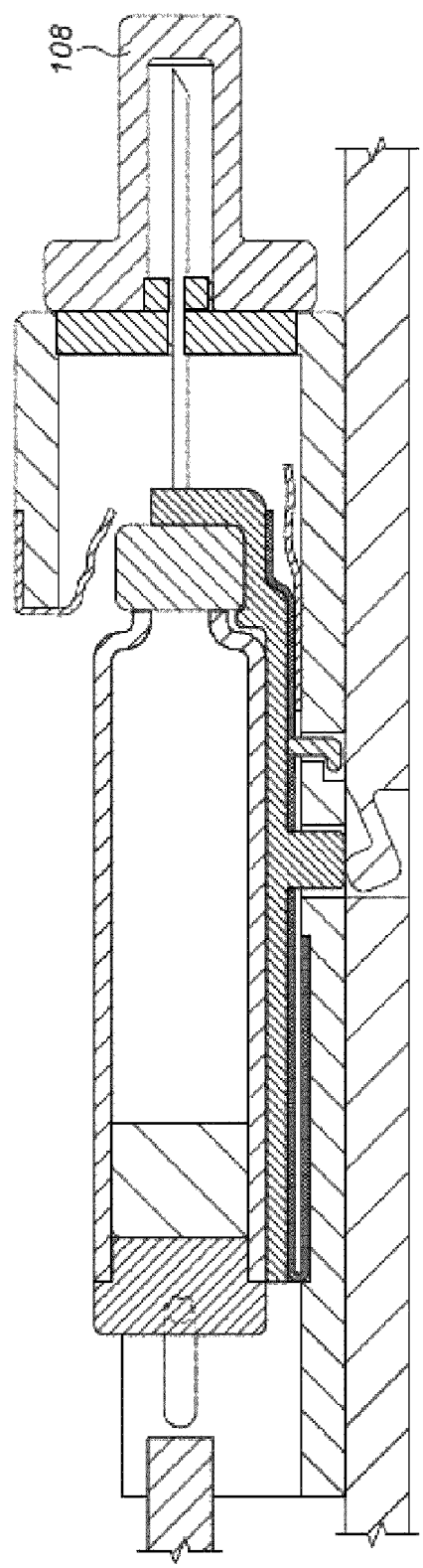
FIG. 14 is a simplified cross-sectional view of the device shown in FIG. 13 in the closed.

FIG. 14 shows the device 100 after the pivotable cartridge holder 101 has been closed. The cartridge holder 101 may be provided with slits (not shown) to enable the neck thereof to fit through the carrier 103 to reach the position shown in FIG. 14. The hook 104 is received by the recess 105 to secure the pivotable cartridge holder 101 to the carrier 103. The unlocking member 107 pushes the locking member 106 so that it is no longer engaging with the carrier 103. As shown in FIG. 14, the carrier 103 and main body may now move axially with respect to the needle sleeve 14.

The device 100 comprises a cap 108. A user may push the cap axially towards the proximal end of the device 100 to cause the needle to pierce the septum of the cartridge 15. The injection may then be commenced in a manner similar to that discussed with respect to the previous embodiment.

While embodiments of the disclosure have been described with respect to auto-injectors, it should be borne in mind that the disclosure is also applicable to alternative injection devices, for example syringes, pen-injectors, manual injectors, spinal injection systems etc. The mechanism for attaching the needle to the medicament cartridge may be employed in any injection device where it is desirable to keep the needle separate from the medicament until shortly before the injection.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15$^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trullcity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A medicament injection device comprising:
a needle holder holding a needle; and
a pivotable cartridge holder pivotable from an open state to a closed state, wherein the cartridge holder is arranged to receive a medicament cartridge in the open state,
wherein the needle holder is movable in an automated axial movement towards the cartridge holder when the cartridge holder is in the closed state, and
wherein movement of the cartridge holder to the closed state causes the automated axial movement of the needle holder in a proximal direction towards the cartridge holder.

2. The medicament injection device of claim 1, wherein the cartridge holder is pivotable about a bearing axis towards a proximal end of the medicament injection device.

3. The medicament injection device of claim 2, wherein the bearing axis is transverse to a longitudinal axis of the medicament injection device.

4. The medicament injection device of claim 1, further comprising a needle sleeve and a pre-stressed spring coupled to the needle sleeve and the needle holder,
wherein the movement of the cartridge holder to the closed state causes a release of the pre-stressed spring, thereby causing the automated axial movement of the needle holder towards the cartridge holder.

5. The medicament injection device of claim 4, further comprising a cap, wherein the cap is coupled to the needle sleeve and comprises a clip to prevent removal of the cap until the spring is released.

6. The medicament injection device of claim 5, wherein the cap comprises an arm supported on an inner surface by the needle sleeve and on an outer surface by the needle holder so as to prevent the cap from moving axially.

7. The medicament injection device of claim 1, further comprising one or more clips arranged to prevent accidental closure of the cartridge holder.

8. The medicament injection device of claim 1, further comprising a clip configured to secure the cartridge holder to a main body of the medicament injection device subsequent to closing the cartridge holder.

9. The medicament injection device of claim 8, wherein the clip is configured to provide tactile feedback as the cartridge holder is closed.

10. The medicament injection device of claim 1, further comprising a needle shield for protecting a distal end of the needle.

11. The medicament injection device of claim 1, further comprising a solid foil for protecting a proximal end of the needle.

12. The medicament injection device of claim 11, further comprising a compressible spacer to protect the solid foil.

13. The medicament injection device of claim 1, wherein the cartridge holder contains the medicament cartridge containing a medicament.

14. The medicament injection device of claim 1, wherein the medicament injection device is an auto-injector.

15. The medicament injection device of claim 1, comprising a body, wherein the cartridge holder pivots towards the body from the open state to the closed state.

16. A method of loading a medicament injection device comprising a needle holder holding a needle, the method comprising:
inserting a medicament cartridge having a penetrable barrier at one end thereof into a pivotable medicament cartridge holder; and
closing the cartridge holder,
wherein closing the cartridge holder causes an automated axial movement of the needle holder towards the cartridge holder and causes the needle to automatically penetrate the penetrable barrier.

17. The method of claim 16, wherein causing the automated axial movement of the needle holder comprises causing the needle holder to move axially in a proximal direction towards the cartridge holder.

18. The method of claim 16, wherein closing the cartridge holder comprises pivoting the cartridge holder about a bearing axis towards a proximal end of the medicament injection device.

19. The method of claim 16, wherein closing the cartridge holder comprises causing a release of a pre-stressed spring to cause the automated axial movement of the needle holder towards the cartridge holder.

20. The method of claim 19, wherein causing the release of the pre-stressed spring comprises causing compression of a spacer while the needle penetrates the penetrable barrier.

21. The method of claim 16, wherein the medicament injection device comprises a body, and closing the cartridge holder comprises pivoting the cartridge holder towards the body.

* * * * *